US008698883B2

United States Patent
Nakano (10) Patent No.: US 8,698,883 B2
(45) Date of Patent: Apr. 15, 2014

(54) ENDOSCOPIC IMAGE REPRODUCING APPARATUS

(75) Inventor: Sumito Nakano, Akishima (JP)

(73) Assignee: Olympus Corporation, Tokyo (JP)

( * ) Notice: Subject to any disclaimer, the term of this patent is extended or adjusted under 35 U.S.C. 154(b) by 288 days.

(21) Appl. No.: 13/344,105

(22) Filed: Jan. 5, 2012

(65) Prior Publication Data

US 2012/0169858 A1 Jul. 5, 2012

(30) Foreign Application Priority Data

Jan. 5, 2011 (JP) ................................. 2011-000796

(51) Int. Cl.
*H04N 7/18* (2006.01)

(52) U.S. Cl.
USPC ....................................... 348/65; 348/E7.085

(58) Field of Classification Search
CPC .......................... A61B 1/00002; A61B 1/00006
USPC ............................................... 348/65, E7.085
See application file for complete search history.

(56) References Cited

U.S. PATENT DOCUMENTS

2010/0076263 A1 * 3/2010 Tanaka et al. ................. 600/109

FOREIGN PATENT DOCUMENTS

JP 2008-133687 A 6/2008

* cited by examiner

*Primary Examiner* — Huy T Nguyen
(74) *Attorney, Agent, or Firm* — Dickstein Shapiro LLP (57) ABSTRACT

An endoscopic image reproducing apparatus has an image pickup section that picks up an image of an object, an image generating unit that generates image data based on an image signal, an acceleration measuring section that measures accelerations of the image pickup section, a moving image file generating section that generates a moving image file including the image data and the acceleration data, a reading section that reads the image data and the acceleration data from the moving image file, a calculating section that calculates a position and a direction of the image pickup section at a certain time of a moving image based on an acceleration, an associating section that associates the position and direction of the image pickup section with the image data at that time, and an insertion path calculating section that calculates an insertion path based on the position of the image pickup section.

5 Claims, 8 Drawing Sheets

| | STRUCTURE | | | DATA | COMMENT | |
|---|---|---|---|---|---|---|
| RIFF "AVI" (31) | | | | "RIFF" | | 30 |
| | | | | * * * * | FILE SIZE | |
| | | | | "AVI" | | |
| | LIST "hdrl" | | | "LIST" | | |
| | | | | * * * * | SIZE | |
| | | | | "hdrl" | | |
| | | avih (35) | | "avih" | AVI MAIN HEADER | |
| | | | | * * * * | SIZE | |
| | | | | : | HEREINAFTER, MAIN HEADER INFORMATION | |
| | | LIST "strl" (36) | | "LIST" | | |
| | | | | * * * * | SIZE | |
| | | | | "strl" | | |
| | | | strh | "strh" | AVI STREAM HEADER (FOR VIDEO DATA) | |
| | | | | * * * * | SIZE | |
| | | | | "vids" | KIND OF STREAM (VIDEO) | |
| | | | | : | HEREINAFTER, STREAM HEADER INFORMATION | |
| | | | strf | "strf" | STREAM FORMAT | |
| | | | | * * * * | SIZE | |
| | | | | : | HEREINAFTER, FORMAT INFORMATION | |
| | | | strn | "strn" | OPTION DATA | |
| | | | | * * * * | SIZE | |
| | | | | : | HEREINAFTER, OPTION DATA CONTENTS | |
| | | LIST "strl" (37) | | "LIST" | | |
| | | | | * * * * | SIZE | |
| | | | | "strl" | | |
| | | | strh (38) | "strh" | AVI STREAM HEADER (FOR AUDIO DATA) | |
| | | | | * * * * | SIZE | |
| | | | | "auds" | KIND OF STREAM (AUDIO) | |
| | | | | : | HEREINAFTER, STREAM HEADER INFORMATION | |
| | | | strf (39) | "strf" | STREAM FORMAT | |
| | | | | * * * * | SIZE | |
| | | | | : | HEREINAFTER, FORMAT INFORMATION | |
| | | | strn (40) | "strn" | OPTION DATA | |
| | | | | * * * * | SIZE | |
| | | | | : | HEREINAFTER, OPTION DATA CONTENTS ADDED INFORMATION FLAG | |
| JUNK (32) | | | | "JUNK" | DUMMY CHUNK TO MAKE 2048 BYTE BOUNDARY | |
| | | | | * * * * | SIZE | |
| | | | | 0 (ALL) | JUNK DATA | |
| LIST "movi" (33) | | | | "LIST" | | |
| | | | | * * * * | SIZE | |
| | | | | "movi" | | |
| 33a | 41a | 00dc (JPEG DATA) #01 | | "00dc" | | |
| | | | | * * * * | SIZE | |
| | | | | % % % % | FRAME DATA | A |
| | | : | | | | |
| | 41a | 00dc (JPEG DATA) #30 | | "00dc" | | |
| | | | | * * * * | SIZE | |
| | | | | % % % % | FRAME DATA | |
| | 42a | 00as (ACCELERATION SENSOR DATA) #01 | | "00as" | | |
| | | | | * * * * | SIZE | B |
| | | | | % % % % | FRAME DATA | |
| 33b | 41b | 00dc (JPEG DATA) #31 | | "00dc" | | |
| | | | | * * * * | SIZE | |
| | | | | % % % % | FRAME DATA | |
| | | : | | | | |
| | 41b | 00dc (JPEG DATA) #60 | | "00dc" | | |
| | | | | * * * * | SIZE | |
| | | | | % % % % | FRAME DATA | |
| | 42b | 00as (ACCELERATION SENSOR DATA) #02 | | "00as" | | |
| | | | | * * * * | SIZE | |
| | | | | % % % % | FRAME DATA | |
| | | : | | | | |
| (34) | idx1 | | | "idx1" | INDEX FOR SPECIFYING REPRODUCTION SEQUENCE | |
| | | | | * * * * | SIZE | |
| | | | | : | HEREINAFTER, INDEX | |

FIG.3

| 00as (ACCELERATION SENSOR DATA) #01 | "00as" | |
|---|---|---|
| | * * * * | SIZE |
| | nnnn | SAMPLING FREQUENCY |
| | h : mm : ss : fff | SAMPLING TIME |
| | x0001 | X-AXIS ACCELERATION SENSOR VALUE |
| | y0001 | Y-AXIS ACCELERATION SENSOR VALUE |
| | z0001 | Z-AXIS ACCELERATION SENSOR VALUE |
| | h : mm : ss : fff | SAMPLING TIME |
| | x0002 | X-AXIS ACCELERATION SENSOR VALUE |
| | y0002 | Y-AXIS ACCELERATION SENSOR VALUE |
| | z0002 | Z-AXIS ACCELERATION SENSOR VALUE |
| | ... | |
| | h : mm : ss : fff | SAMPLING TIME |
| | xnnnn | X-AXIS ACCELERATION SENSOR VALUE |
| | ynnnn | Y-AXIS ACCELERATION SENSOR VALUE |
| | znnnn | Z-AXIS ACCELERATION SENSOR VALUE |

IMAGE PICKUP SECTION POSITION TABLE

| TIME | ACCELERATION SENSOR VALUE (cm/sec^2) | | | SPEED (cm/sec) | | | POSITION (cm) | | | MOVING IMAGE FRAME |
|---|---|---|---|---|---|---|---|---|---|---|
| | X | Y | Z | X | Y | Z | X | Y | Z | |
| 0:00:00.000 | 0.0020 | 0.0031 | 0.1246 | 0.000 | 0.000 | 0.000 | 0.00 | 10.00 | 0.00 | 1 |
| 0:00:00.017 | 0.0055 | 0.0069 | 0.1209 | 0.000 | 0.000 | 0.002 | 0.00 | 10.00 | 0.00 | 1 |
| 0:00:00.033 | 0.0021 | 0.0089 | 0.1196 | 0.000 | 0.000 | 0.004 | 0.00 | 10.00 | 0.00 | 2 |
| 0:00:00.050 | 0.0044 | 0.0073 | 0.1180 | 0.000 | 0.000 | 0.006 | 0.00 | 10.00 | 0.00 | 2 |
| 0:00:00.067 | 0.0035 | 0.0095 | 0.1151 | 0.000 | 0.000 | 0.008 | 0.00 | 10.00 | 0.00 | 3 |
| 0:00:00.083 | 0.0033 | 0.0106 | 0.1157 | 0.000 | 0.001 | 0.010 | 0.00 | 10.00 | 0.00 | 3 |
| 0:00:00.100 | 0.0033 | 0.0087 | 0.1123 | 0.000 | 0.001 | 0.012 | 0.00 | 10.00 | 0.00 | 4 |
| 0:00:00.117 | 0.0008 | 0.0068 | 0.1097 | 0.000 | 0.001 | 0.014 | 0.00 | 10.00 | 0.00 | 4 |
| ... | | | | | | | | | | |
| 0:01:03.000 | 0.0058 | −0.0077 | 0.0016 | −0.144 | 0.033 | 3.254 | 63.55 | 42.10 | 98.73 | n |

ENDOSCOPIC IMAGE REPRODUCING APPARATUS

CROSS REFERENCE TO RELATED APPLICATION

This application claims benefit of Japanese Application No. 2011-000796 filed in Japan on Jan. 5, 2011, the contents of which are incorporated by this reference.

BACKGROUND OF THE INVENTION

1. Field of the Invention

The present invention relates to an endoscopic image reproducing apparatus, and particularly relates to an endoscopic image reproducing apparatus that can determine at which position and from which direction of an object to be examined an endoscopic image is photographed.

2. Description of the Related Art

Conventionally, endoscope apparatuses which include an endoscope that obtains an observed image by inserting an insertion portion into an object to be observed, and a display section that displays the observed image, have been generally used. The objects to be observed include the interiors of structures such as piping and engines, besides the interiors of body cavities. Especially at the time of inspection of the interior of piping, an endoscope that has a long insertion portion is used. When the shape of piping is complicated and long, it is difficult to find the position and the direction of the distal end of the insertion portion as the endoscope is inserted.

Japanese Patent Application Laid-Open Publication No. 2008-133687 discloses an art that can grasp the position and the direction of the distal end of an insertion portion by mounting a triaxial acceleration sensor at the distal end of the insertion portion and providing an insertion distance detecting section that measures a moving length of the distal end of the insertion portion.

Meanwhile, in an actual inspection of the object to be examined such as piping, an inspector sometimes does not perform a detailed inspection at an inspection site, but photographs a general image of the object to be examined and only records the image as a moving image file by using a moving image recording function, due to time constraints, and thereafter, reproduces the image file to perform a detailed inspection.

SUMMARY OF THE INVENTION

An endoscopic image reproducing apparatus according to one aspect of the present invention has an image generating unit that generates image data based on an image pickup signal picked up by an image pickup section that picks up an image of an object to be examined by an optical system and an image pickup device that are provided in a distal end of an endoscope insertion portion, a moving image file generating section that generates a moving image file by successively recording in a storage medium both the image data generated by the image generating unit and acceleration data measured by an acceleration measuring section that measures triaxial accelerations of the image pickup section, a reading section that reads the image data and the acceleration data from the moving image file that is recorded in the storage medium, a calculating section that calculates a position and a direction of the image pickup section at a certain time point of a moving image based on the acceleration data, an associating section that associates the calculated position and direction of the image pickup section at the certain time point of the moving image with the image data at the time point, and an insertion path calculating section that calculates an insertion path in a certain range of the moving image based on the position of the image pickup section that the calculating section calculates.

DETAILED DESCRIPTION OF THE PREFERRED EMBODIMENTS

An embodiment of the invention will be described with reference to the drawings.

[Configuration]

Figure 1:
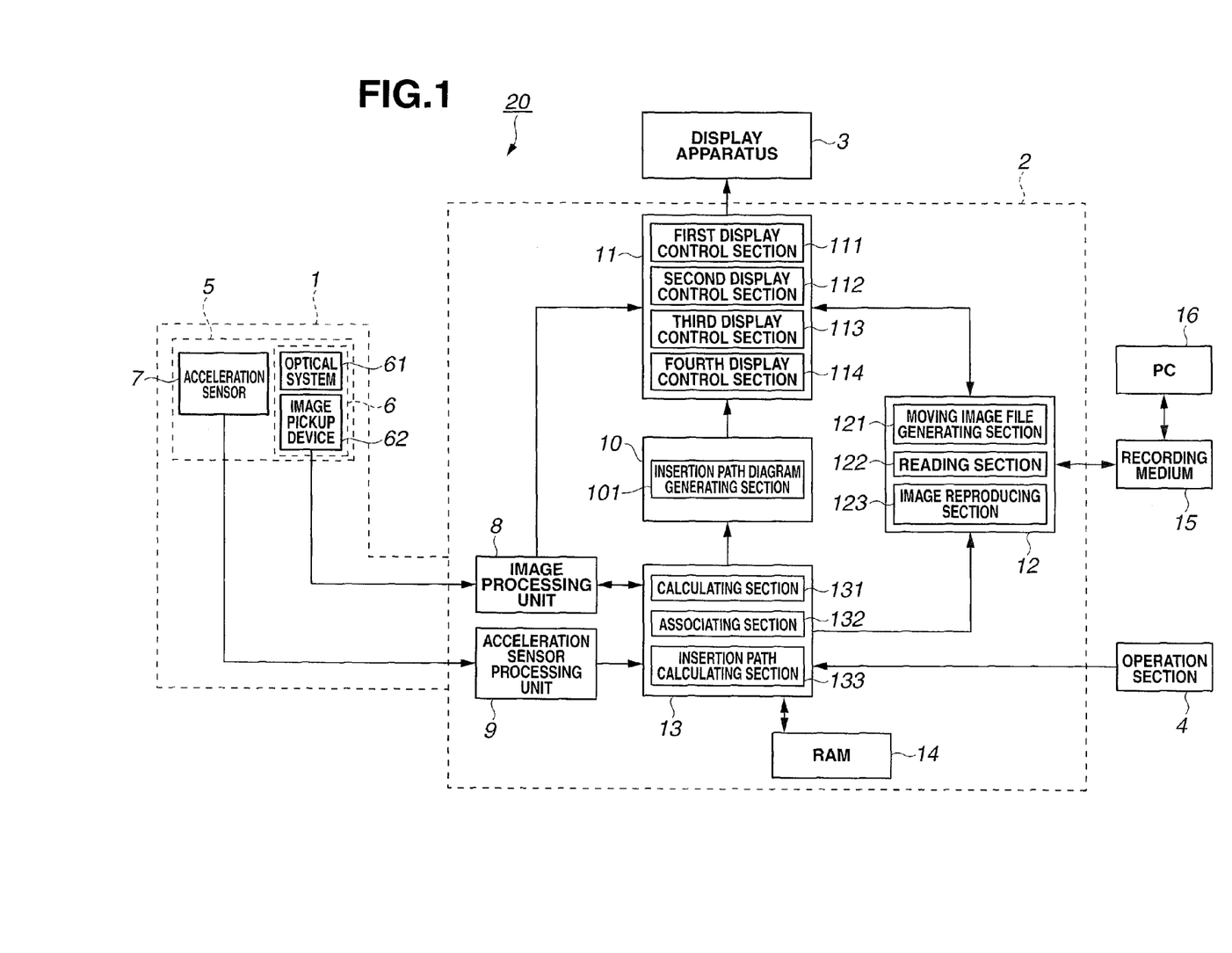
FIG. 1 is a block diagram showing a configuration of an endoscope apparatus of one embodiment of the present invention.

FIG. 1 is a block diagram showing a configuration of an endoscopic image reproducing apparatus of one embodiment of the present invention.

In FIG. 1, an endoscopic image reproducing apparatus 20 includes an insertion portion 1, a main body section 2, a display apparatus 3, an operation section 4, a RAM 14, a recording medium 15 and a personal computer (hereinafter, PC) 16. The operation section 4 also includes a function as a position specifying section.

The insertion portion 1 is constructed with a long cylindrical body that can be inserted into a pipe line of piping, and includes a distal end portion 5 at a distal end part of the endoscope insertion portion 1.

The distal end portion 5 includes an image pickup section 6 that picks up an image of an object to be examined by an optical system 61 provided at a distal end of the endoscope insertion portion and an image pickup device 62 such as a CCD, and photoelectrically converts the image of the object to be examined incident on an image pickup surface to generate an image pickup signal, and an acceleration sensor 7 as an acceleration measuring section that measures triaxial accelerations of the image pickup section.

Measurement of the triaxial accelerations by the acceleration sensor 7 also can be carried out in a process of extraction of the image pickup section 6 out of a pipe line, besides being carried out in a process of inserting the image pickup section 6 into the pipe line.

The main body section 2 includes an image processing unit 8 as an image generating unit, an acceleration sensor processing unit 9, a graphic generating unit 10, an image synthesizing unit 11, a recording medium reading and writing unit 12, and a main control unit 13. The graphic generating unit 10 also includes the function as an insertion path diagram generating unit. CAD data that is a design drawing or an installation drawing of piping is recorded in advance in a recording medium 15.

The above described image processing unit 8 generates image data of a moving image based on the image pickup signal of an image picked up by the image pickup section 6. The image processing unit 8 receives the image pickup signal outputted from the image pickup section 6 which is contained in the distal end portion 5 of the insertion portion 1, applies image processing such as gamma correction processing, edge enhancement processing and digital zoom processing, for example, to the image pickup signal, and generates endoscopic image data of the moving image. The image processing unit 8 supplies the generated endoscopic image data to the image synthesizing unit 11.

Further, the insertion portion 1 includes, in the distal end portion 5, the acceleration sensor 7 that detects information (hereinafter, acceleration data) concerning an acceleration of the image pickup section 6 in the distal end portion 5.

The acceleration sensor 7 is, for example, a triaxial acceleration sensor, and outputs a signal corresponding to the detected acceleration data of the image pickup section 6, that is, acceleration values in triaxial directions of the image pickup section 6 in the distal end portion 5, to the acceleration sensor processing unit 9. The triaxial acceleration sensor obtains the magnitudes of the accelerations in the triaxial directions in the three-dimensional space by using three sensors in which respective detection axes of an X-axis, a Y-axis and a Z-axis are orthogonal to one another, and synthesizes the magnitudes of the triaxial accelerations as vector components to be able to detect the direction in which the acceleration is applied and the magnitude.

The acceleration sensor processing unit 9 receives an acceleration data signal of the image pickup section 6 in the distal end portion 5, which is outputted from the acceleration sensor 7. The acceleration sensor processing unit 9 receives the acceleration data signal, converts the acceleration data signal into acceleration information representing an inclination angle or the like with respect to a gravity (vertical) direction, and supplies the converted acceleration information to the main control unit 13.

In the main control unit 13, a value of an image pickup section position table (see FIG. 6) is calculated at a reproduction time based on the supplied data of the acceleration sensor, a position of the image pickup section is plotted on three-dimensional space coordinates according to the data of the image pickup section position table, and an insertion path f (see FIG. 8) is obtained. The data of the insertion path f is supplied to the graphic generating unit 10 from the main control unit 13.

The graphic generating unit 10 includes an insertion path diagram generating section 101. The graphic generating unit 10 generates data of the insertion path f that is calculated based on the position inside a pipe line, of the image pickup section 6 in the distal end portion 5, and an insertion path diagram 71 representing a direction of the image pickup section on the insertion path f by using an indicator g. The data of the insertion path diagram 71 from the graphic generating unit 10 is supplied to the aforementioned image synthesizing unit 11, synthesized, and displayed on the same screen as the moving image data from the aforementioned image processing unit 8, and/or recorded.

Figure 9:
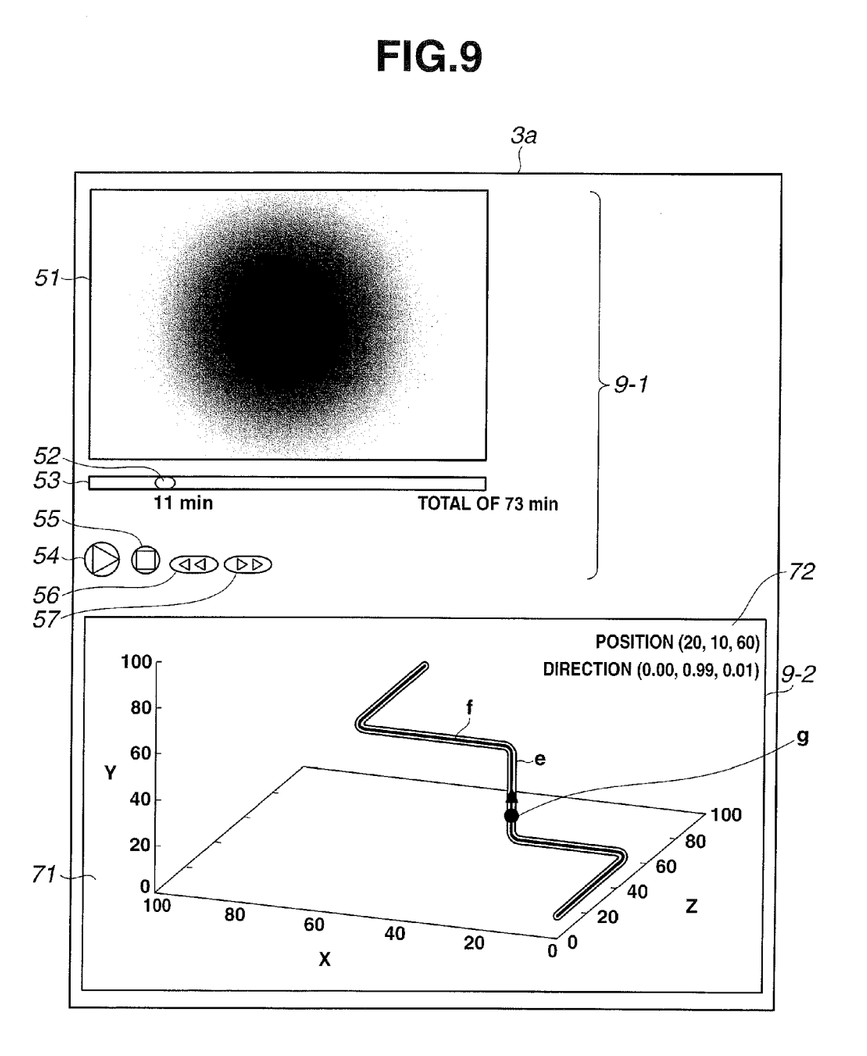
FIG. 9 is a diagram showing a state in which a moving image frame of an endoscopic image that is picked up in a pipe line, and an insertion path diagram showing an insertion path in the pipe line in which the image pickup section that picks up an image of the moving image frame is inserted are displayed on a screen.

The graphic generating unit 10 generates the indicator g as shown in FIG. 9 as the data showing the direction at the position of the image pickup section on the insertion path f.

The above described image synthesizing unit 11 includes a first display control section 111, a second display control section 112, a third display control section 113 and a fourth display control section 114.

The first display control section 111 includes a function of displaying only the insertion path diagram 71. The second display control section 112 includes a function of acquiring, with an associating section 132, the position and the direction of the image pickup section at a time point when the reproduced image data is photographed, and displaying both the image data and the insertion path diagram data. The third display control section 113 includes a function of displaying image data associated with a certain position on the insertion path. The fourth display control section 114 includes a function of displaying both the insertion path f (see FIG. 9) generated by the graphic generating unit 10 as the insertion path diagram generating unit, and a pipe shape e based on design drawing data showing the shape of an object to be examined which is obtained from CAD data.

The image synthesizing unit 11 generates the insertion path diagram 71 (see FIG. 9) in which the insertion path f is superimposed on the pipe shape e (see FIG. 4) of the object to be examined that is created from the CAD data corresponding to a design diagram by the fourth display control section 114. By the second display control section 112, the insertion path diagram 71 and the moving image frame 51 are synthesized, and a synthetic image including an image display region 9-1 and an insertion path diagram display region 9-2 as shown in FIG. 9 is generated and displayed on a display section 3a.

The image synthesizing unit 11 also can perform processing for individually displaying an endoscopic image on the display apparatus 3 in accordance with control by the main control unit 13.

The above described recording medium reading and writing unit 12 includes a moving image file generating section 121, a reading section 122, and an image reproducing section 123.

The moving image file generating section 121 includes a function of generating a moving image file by successively recording both the image data generated by the image processing unit 8 and the acceleration data that is measured by the acceleration sensor 7 in the recording medium 15. The reading section 122 includes a function of reading image data and acceleration data from the moving image file recorded in the recording medium 15. The moving image reproducing section 123 includes a function of reproducing a moving image or an image in the moving image.

The recording medium 15 such as a flash memory, for example, is detachably connected to the recording medium reading and writing unit 12. In a state in which the recording medium 15 is fitted to the recording medium reading and writing unit 12, the recording medium reading and writing unit 12 reads the endoscopic image data and the data of the insertion path diagram 71 that are supplied to the image synthesizing unit 11 in accordance with control from the main control unit 13 based on a recording instruction from the operation section 4, and supplies the data to the recording medium 15 as one moving image file and records the data. As a moving image file, for example, an AVI file in a Motion JPEG format is used.

The operation section 4 is provided with operation switches or the like not illustrated for performing a bending operation of the distal end portion 5, a recording operation to the recording medium 15 described above, and the like, and an inspector operates the operation switch of the operation section 4, and performs desired operations such as a bending operation, a recording operation and the like. The operation section 4 supplies an operation signal corresponding to the operation of the inspector to the main control unit 13.

The above described main control unit 13 controls each of circuit portions and the like to perform processing corresponding to the operation signal from the operation section 4, and performs operation control of the entire endoscopic image reproducing apparatus 20.

The main control unit 13 includes a calculating section 131 that calculates a position and a direction of the image pickup section 6 at a certain time point in a moving image based on an acceleration, the associating section 132 that associates the calculated position and direction of the image pickup section 6 at a certain time point in the moving image with the image at the time point, and an insertion path calculating section 133 that calculates an insertion path in a certain range of the moving image based on the position of the image pickup section 6 calculated by the calculating section 131.

The operation section 4 is also used as a position specifying section that specifies the image pickup section position in the insertion path diagram 71 (see FIG. 9) by moving the image pickup section position indicator g as a cursor on the insertion path f which is displayed. In this case, a moving image frame 51 on the display screen also changes in response to the change of the position of the indicator g on the insertion path f, and the position of a slider 52 on a reproduction bar 53 also changes. The indicator g has a predetermined length, and also includes a function of showing a photographing direction at a certain position of the image pickup section.

Next, an operation of the endoscopic image reproducing apparatus of FIG. 1 will be described. The operation of the endoscopic image reproducing apparatus will be described with reference to any of FIG. 2 and the following drawings.

[Photographing and Recording Operation]

The distal end part (including the image pickup section 6) of the endoscope insertion portion 1 is inserted into the pipe line of piping that is an object to be examined, and thereby, the image pickup section 6 moves inside the pipe line at a substantially constant speed and picks up an image of the inside of the pipe line. At this time, photographing of a moving image is performed while the image pickup section 6 is moved over a certain range of the pipe line from an insertion end of the pipe line. The image pickup signal of the image that is picked up is subjected to image processing in the image processing unit 8, and recorded in the recording medium 15 as endoscopic image data. In this recording operation, a moving image frame of the endoscopic image data and acceleration data from the acceleration sensor 7 are associated with each other by the associating section 132 in the main control unit 13, and thereafter, the moving image frame and acceleration data that are associated with each other are recorded in the recording medium 15 as the moving image file by the recording medium reading and writing unit 12.

[Reproducing Operation]

Figure 6:
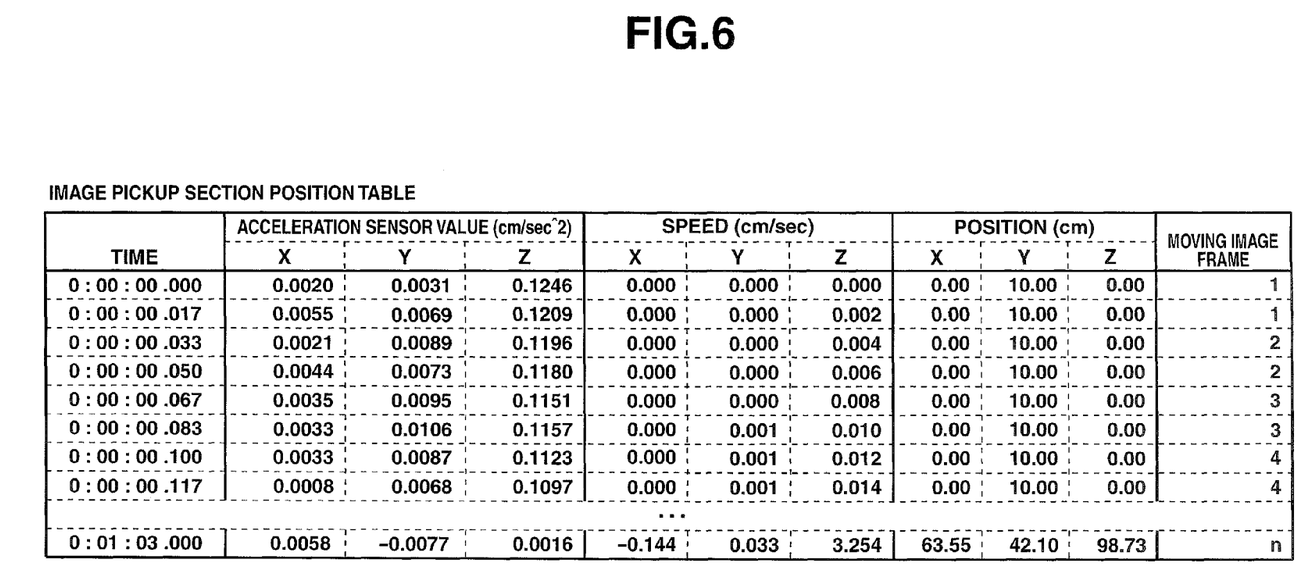
FIG. 6 is a diagram showing an image pickup section position table.
Figure 7:
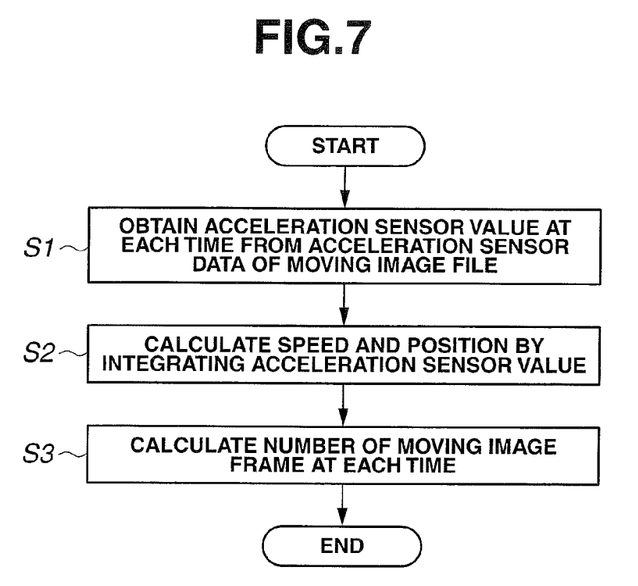
FIG. 7 is a flowchart of creating the image pickup section position table of FIG. 6.

When an inspector opens the moving image file by an operation of opening the moving image file of the recording medium 15 or the like by an operation of the operation section 4 after the above described recording operation, the main control unit 13 controls the reading section 122 by processing of a flowchart of FIG. 7, and reads the image data and the acceleration data from the aforementioned moving image file that is recorded in the aforementioned recording medium 15. FIG. 7 will be described later. Thereafter, the main control unit 13 calculates a photographing position and a photographing direction of the image pickup section 6 in the pipe line as shown in FIG. 6 by controlling the calculating section 131 and integrating acceleration values of the acceleration data, and creates an image pickup section position table. The image pickup section position table is stored in the recording medium 15 after being created. Subsequently, the photographing directions of the image pickup section 6 at the positions are also calculated with use of the position data of the created image pickup section position table. Further, the main control unit 13 controls the insertion path calculating section 133, calculates the insertion path f in a certain range of the moving image based on the position of the image pickup section 6 which is calculated, and displays the insertion path f on the display section 3a with the moving image frame 51. The insertion path f is stored in the recording medium 15 with use of the recording medium reading and writing unit 12 after being calculated.

In the recording medium 15, CAD data that is a design drawing of the piping is recorded in advance, and the insertion path f of the image pickup section 6 in the pipe line is superimposed on the pipe shape e of the design drawing, and is displayed on the screen of the display section 3a.

Simultaneously with reproduction of the moving image frame 51, the image pickup section position indicator g as a cursor is displayed on the insertion path f. In the indicator g, a point (•) indicates the position of the image pickup section, and an arrow (↑) of a predetermined length indicates the photographing direction of the image pickup section. The indicator g moves on the insertion path f of the image pickup section 6 with a lapse of time by being linked with reproduction of the moving image frame 51. That is, in response to the movement of the indicator position, the moving image frame 51 which is a moving image of the inside of the pipe line photographed is sequentially displayed, and at the same time, the slider 52 that indicates a temporal reproduction position on the reproduction bar 53 shown in FIG. 9 also moves on the reproduction bar.

Calculation of the image pickup section position table that is performed at the time of the reproduction operation may be performed at photographing time and recording operation time. That is, the moving image data and the acceleration data are recorded in the recording medium 15 as the moving image file at the photographing time and recording operation time, and thereafter, the speed and the position data of the image pickup section position table may be calculated and stored in the recording medium 15.

The display section 3a can display the states other than the display state shown in FIG. 9 by the first to the fourth display control sections 111 to 114 that configure the image synthesizing unit 11. The main control unit 13 can display only the insertion path diagram 71 on the screen by controlling the first display control section 111. Further, the main control unit 13 can display both the moving image frame 51 and the insertion path diagram 71 on the same screen by controlling the second display control section 112. Further, the main control unit 13 can display the moving image frame 51 corresponding to the image pickup section position on the insertion path f by controlling the third display control section 113. Further, the main control unit 13 can display both the insertion path f and the pipe shape e based on the design drawing data on the screen by superimposing the insertion path f and the pipe shape e on each other by controlling the fourth display control section 114.

As above, according to the present embodiment, it can be easily grasped that the image data at a certain time point in the moving image is the result of photographing which portion of the object to be examined from which direction, and inspection of the inside of the pipe line with excellent operability, visibility and convenience can be carried out.

Next, a structure of an AVI file that is recorded in the recording medium 15 will be described with reference to FIG. 2.

Figure 2:
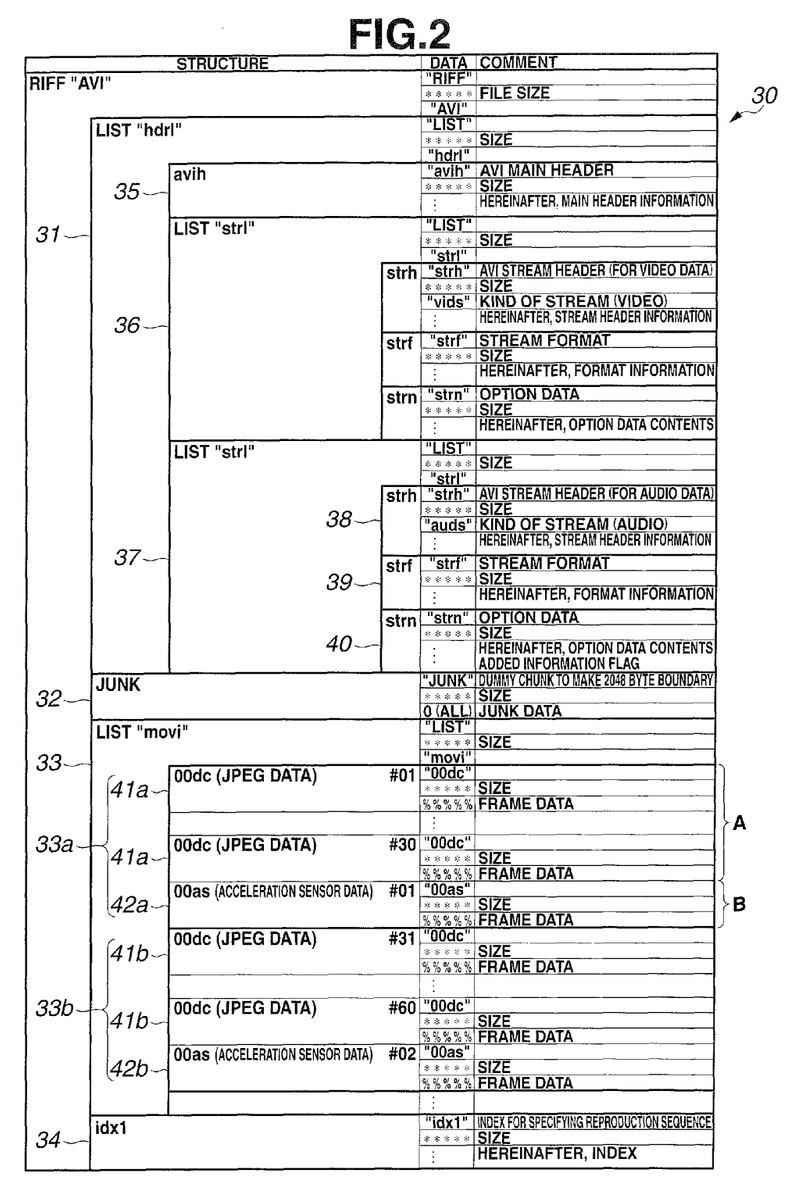
FIG. 2 is a diagram for explaining an example of a structure of an AVI file.

FIG. 2 is a diagram for explaining an example of the structure of the AVI file.

As shown in FIG. 2, an AVI file 30 is in a format called RIFF (Resource Interchange File Format), and has a structure having a header section 31 shown by LIST "hdrl", a dummy chunk 32 shown by JUNK, a stream data section 33 shown by LIST "movi", and an index 34 shown by idx1, in sequence from a head of the file.

The header section 31 has a structure having an AVI main header 35 shown by Avih, a stream list 36 for video data shown by LIST "strl", and a stream list 37 for audio data shown by LIST "strl".

The stream list 37 for audio data has a structure having an AVI stream header 38 shown by strh, a stream format 39 shown by strf and an option data 40 shown by strn.

In the present embodiment, an added information flag is added to an option data content of the option data 40 of the header section 31. The added information flag is a flag showing whether or not acceleration information is stored in the AVI file 30. When the data of the acceleration sensor is not stored in the AVI file 30, the flag information of the added information flag is set to 0, whereas when the acceleration information is stored in the AVI file 30, the flag information of the added information flag is set to 1. The flag information of the added information flag is set by the recording medium reading and writing unit 12 in accordance with control of the main control unit 13.

Further, the stream data section 33 has a structure having a plurality of, in this case, two stream data 33a and 33b divided at each unit time. In FIG. 2, only the two stream data 33a and 33b are illustrated, but the stream data corresponding to the photographing time of the moving image are stored in the stream data section 33. That is, when the moving image of 60 seconds is recorded in the AVI file 30, the stream data section 33 has 60 stream data. The configuration of each of the stream data is the same, and therefore, the configuration of the stream data 33a will be described as an example hereinafter. In a range of reference character A assigned to the right side of the stream data section 33, JPEG data of one second for each frame is stored, and in a range of reference character B, an acceleration sensor value of one second is stored.

The stream data 33a as a stream data region is configured by 30 image streams 41a that are image storing regions, and further, when the acceleration information is added, a region of an information stream 42a that is an information storage region is ensured. When the acceleration information is added, the acceleration information is stored in the region of the information stream 42a. The data of the endoscopic image is stored in the image stream 41a, and the acceleration information corresponding to the data of the endoscopic image is stored in the information stream 42a.

30 image streams 41a are stored in the stream data 33a per unit time, that is, the frame rate is 30, but the frame rate is not restricted to 30, but may be, for example, 24.

Further, the stream data 33a is provided with one information stream 42a, but may be provided with two or more information streams. For example, the stream data 33a per unit time is provided with 30 information streams corresponding to the respective 30 image streams 41a. Subsequently, the acceleration information corresponding to the 30 image streams 41a is stored in the respective regions of the 30 information streams. Thereby, 30 pieces of acceleration information corresponding to the 30 frame data are displayed, and therefore, accurate acceleration information can be displayed.

Further, in the present embodiment, an endoscopic image and acceleration information are stored and saved in one AVI file 30. For example, when voluminous moving image files are present, if the data of endoscopic images and acceleration information are saved in separate files, copying and moving the files are troublesome. Further, when voluminous moving image files are present, if the data of endoscopic images and acceleration information are saved in separate files, omissions of copying, moving or the like of the files may occur. That is, if there is a copy omission or the like in either one of the file of the data of an endoscopic image and the file of acceleration information, a detailed inspection cannot be performed. In contrast with this, in the present embodiment, an endoscopic image and acceleration information are recorded in one AVI file 30, and therefore, occurrence of a copy omission or the like of the file can be prevented, and management of the file is facilitated.

The format of the moving image file is not restricted to the AVI file 30, but may be an MOV file or the like. The MOV file is configured by track units, and can include a text track, a chapter track and the like. For example, acceleration information can be recorded in the text track or the chapter track.

The AVI file 30 recorded in the recording medium 15 like this can be reproduced by the endoscopic image reproducing apparatus 20 as described above, but when the inspector brings the recording medium 15 back to an office or the like, and performs a detailed inspection, it is troublesome to carry the heavy endoscopic image reproducing apparatus 20 together. Thus, the inspector can bring only the recording medium 15 back to the office or the like, reproduce the AVI file 30 recorded in the recording medium 15 with the reproducing apparatus configured by a PC not illustrated, perform a detailed inspection and create an inspection report corresponding to a detailed inspection result.

Figure 3:
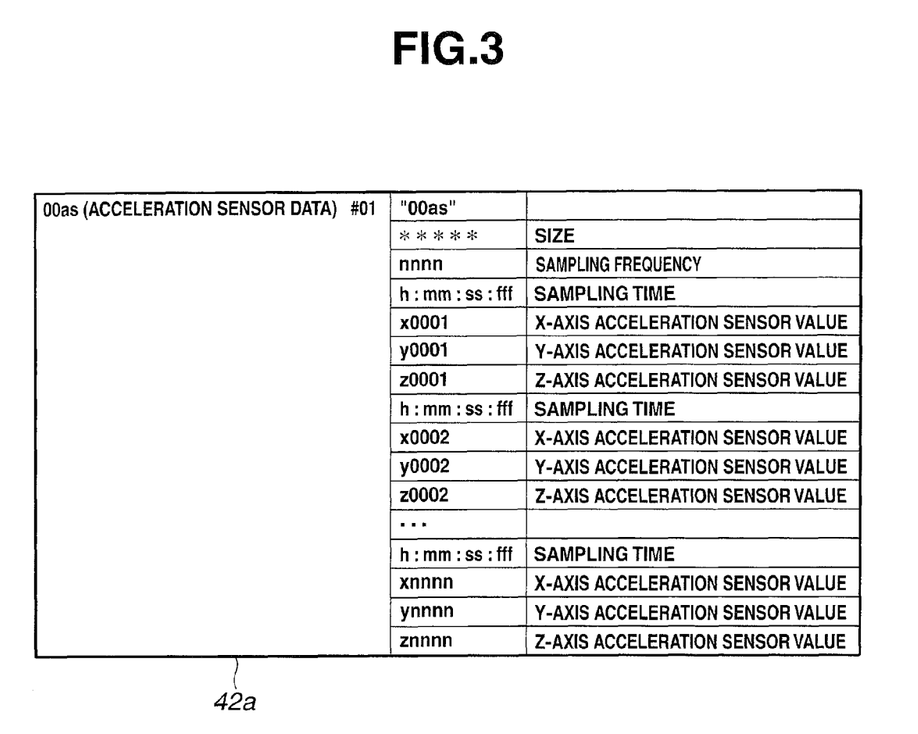
FIG. 3 is a diagram showing a detailed structure of acceleration sensor data that is stored in a moving image file in the AVI file of FIG. 2.

FIG. 3 shows a detailed structure of acceleration sensor data that is stored in the moving image file in the AVI file of FIG. 2. For example, a configuration example of the acceleration sensor data 42a of FIG. 2 is shown.

As the acceleration sensor data, a size, a sampling frequency, a sampling time, an X-axis acceleration sensor value, a Y-axis acceleration sensor value, and a Z-axis acceleration sensor value are included. The sampling frequency per unit time of the acceleration sensor is not necessarily the same as the number of moving image frames per unit time. For example, when the number of image frames is 30 per one second, the sampling frequency per one second of the acceleration sensor may be 60 times that is twice as large as the number of the number of image frames. FIG. 6 shows the case in which the sampling frequency of the acceleration sensor is twice per one moving image frame.

Figure 4:
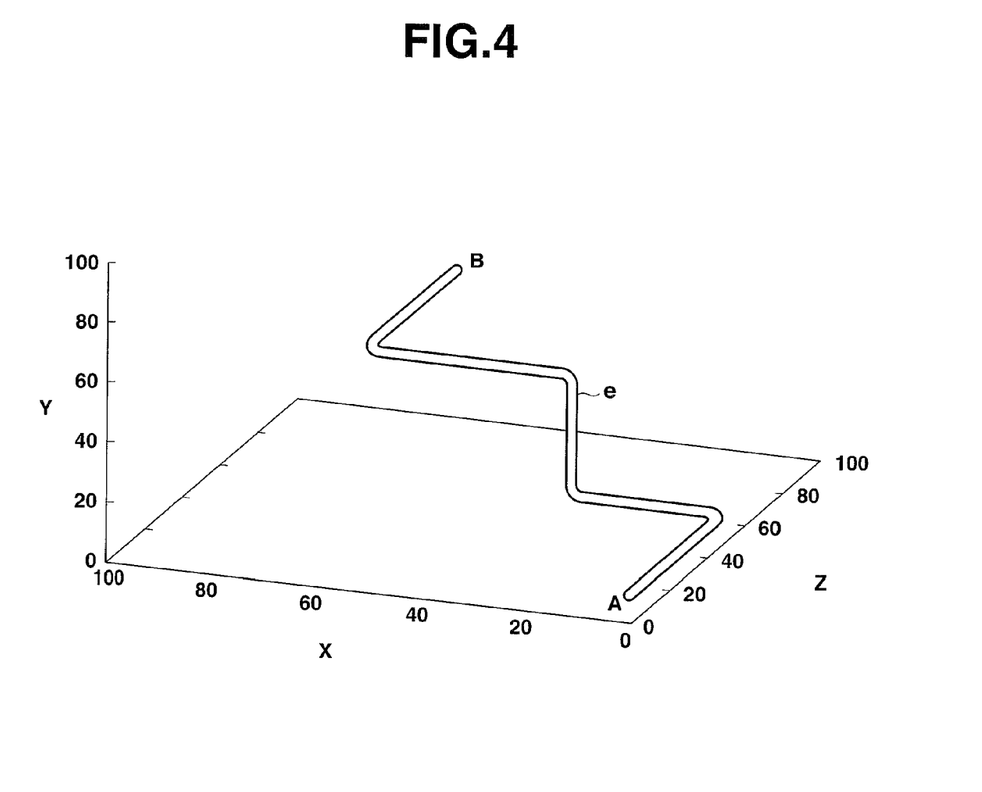
FIG. 4 is a diagram three-dimensionally showing an example of a pipe that is obtained from CAD data used as a design drawing.

FIG. 4 shows an example of the pipe shape e which is obtained from the CAD data that is used as a design drawing. FIG. 4 shows the example of three-dimensionally displaying the pipe shape e in a three-dimensional space by three axes of an X-axis, a Y-axis and a Z-axis.

Figure 5:
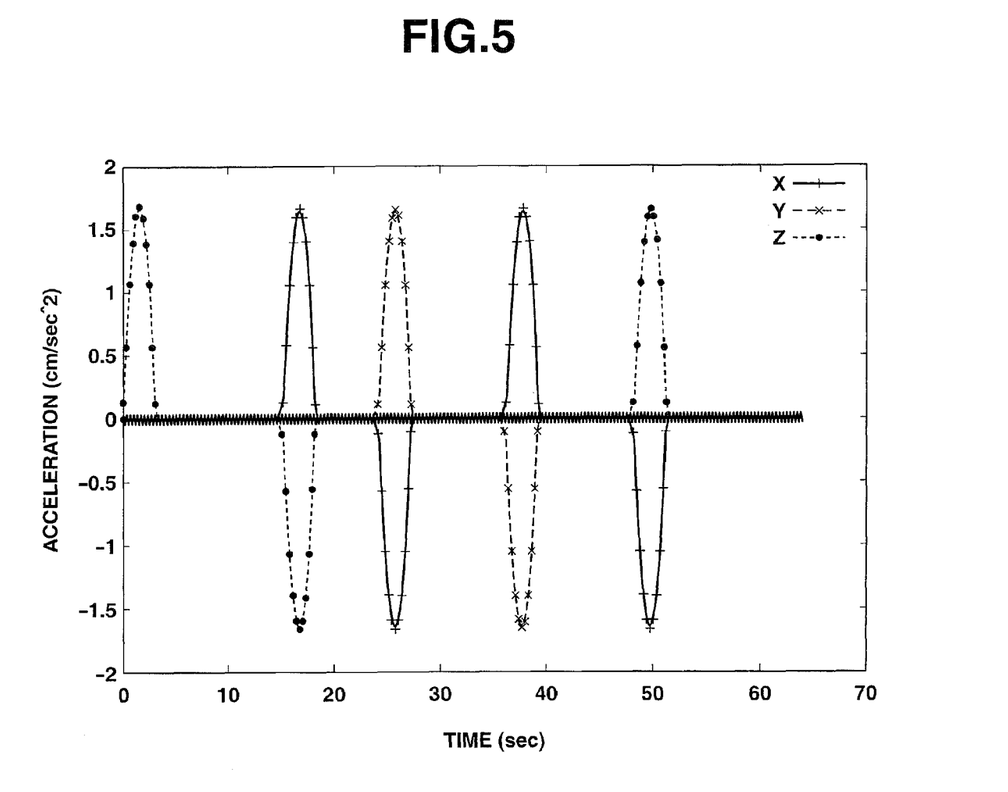
FIG. 5 is a diagram showing an example of values in a triaxial direction of an acceleration sensor that are obtained when the acceleration sensor is inserted from an A-point to a B-point of the pipe shown in FIG. 4.

FIG. 5 is an example of the value of the triaxial acceleration sensor that is obtained when the endoscope is inserted from an A point to a B point of the pipe shown in FIG. 4. When the distal end part of the endoscope insertion portion 1 is inserted to the A-point of the pipe, the Z-axis acceleration value of the image pickup section 6 rapidly increases and decreases in a Z-axis (+) direction in a short time, and thereafter, the image pickup section 6 moves in the Z-axis (+) direction with an acceleration of 0, that is, at a constant speed. Thereafter, the image pickup section 6 reaches a first bending spot, where the Z-axis (−) direction acceleration rapidly increases and decreases, and an X-axis (+) direction acceleration rapidly increases and decreases. Subsequently, the image pickup section 6 moves in the X-axis (+) direction with the acceleration of 0, that is, at a constant speed to reach a second bending spot, where an X-axis (−) direction acceleration rapidly increases and decreases, and a Y-axis (+) direction acceleration rapidly increases and decreases. In the same manner from this point forward, the acceleration of each corresponding axis rapidly changes to increase and decrease especially in the bending spots with movement corresponding to the pipe shape of FIG. 4.

The respective acceleration values in the X, Y and Z-axis directions of the triaxial acceleration sensor are recorded in the moving image file on the recording medium 15 with the image data that is picked up in correspondence with the lapse of time.

When the recording medium reading and writing unit 12 (or a PC 16) that operates based on the control of the main control unit 13 reads the moving image file on the recording medium 15, the recording medium reading and writing unit 12 creates an image pickup section position table as shown in FIG. 6 based on the acceleration sensor data in the moving image file by processing of a flowchart of FIG. 7.

FIG. 6 shows the image pickup section position table, and FIG. 7 shows a flowchart of creating the image pickup section position table of FIG. 6.

First, from the acceleration sensor data of the moving image file, an acceleration sensor value at each time is obtained (step S1). Next, a speed and a position are calculated by integrating the acceleration sensor value (step S2), and the data that is obtained by the calculation is registered in the image pickup section position table. Further, the number of the moving image frame at each time is calculated (step S3). The same number represents the same moving image frame.

Figure 8:
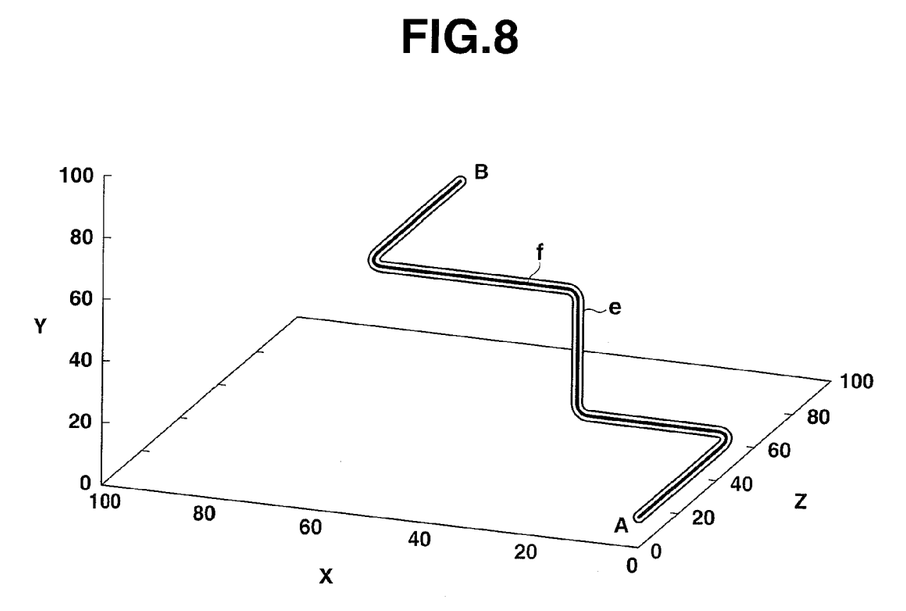
FIG. 8 is a diagram showing a state in which values of positions of the image pickup section position table shown in FIG. 6 are plotted on three-dimensional coordinates, and are superimposed on the pipe of the design drawing shown in FIG. 4.

FIG. 8 shows a state in which the values of the positions of the image pickup section position table shown in FIG. 6 are plotted on three-dimensional coordinates. As a result of plotting, the insertion path f (shown by the thick line) of the endoscope image pickup section is obtained.

In FIG. 8, the above described insertion path f is shown by being superimposed on the pipe shape e of the design drawing of FIG. 4 that is obtained based on the CAD data.

FIG. 9 shows a state in which the moving image frame 51 that is the endoscopic image picked up in the pipe line of piping or the like and an operation button that changes the display state thereof, and the insertion path diagram 71 showing the insertion path in the pipe line in which the image pickup section that picks up an image of the moving image frame is inserted and the position and direction display of the indicator g showing the image pickup section position are displayed on the display section 3a of the display apparatus 3 of the endoscopic image reproducing apparatus 20.

In the display section 3a, reference numeral 9-1 designates the image display region of an endoscopic image, and reference numeral 9-2 designates the insertion path diagram display region. In the image display region 9-1, reference numeral 51 designates the moving image frame, reference numeral 52 designates the slider movable on the reproduction bar 53, reference numeral 53 designates the reproduction bar, reference numeral 54 designates a reproduction button, reference numeral 55 designates a stop button, reference numeral 56 designates a rewind button, and reference numeral 57 designates a fast-forward button. In the insertion path diagram display region 9-2, reference character e designates the pipe that is the pipe line based on the design diagram, reference character f designates the insertion path of the image pickup section that is obtained by plotting of the image pickup section position calculated based on the acceleration data, reference character g designates an image pickup section position indicator that indicates the position on the insertion path f, which corresponds to the image pickup position of the moving image that is displayed at the time of reproduction of the moving image, and reference numeral 72 shows the position and direction display of the position and the direction of the image pickup section position indicator g represented in the coordinates of X, Y and Z.

When the recording medium reading and writing unit 12 (or the PC 16) that operates based on control of the main control unit 13 opens the moving image file on the recording medium 15, the recording medium reading and writing unit 12 creates the image pickup section position table of FIG. 6, calculates the insertion path f, and displays the insertion path f on the display section 3a of the display apparatus 3 with the moving image frame 51.

The image pickup section position indicator g moves along the insertion path f by being linked with the reproduction of the moving image frame 51. The position of the image pickup section position indicator g is acquired from the image pickup section position table of FIG. 6 in accordance with the moving image frame 51 that is displayed. The image pickup section position indicator g can move on the insertion path f by key operation (or mouse operation) of the operation section 4. When the image pickup section position indicator g is moved, the number of the moving image frame in the moving image corresponding to the image pickup section position is acquired from the image pickup section position table, and the reproduction position of the moving image frame is moved.

In the above configuration, the output value of the triaxial acceleration sensor provided at the distal end of the endoscope is recorded in the corresponding moving image file. As shown in FIG. 6, the timing at which the value of the triaxial acceleration sensor is outputted, and the timing of the frame of the moving image are associated with each other.

The output value of the triaxial acceleration sensor recorded in the moving image file is integrated, and thereby the position and the direction of the endoscope distal end are calculated for each frame of the moving image. The direction is obtained from a change of the position coordinates on the triaxial space coordinates by the X-axis, the Y-axis and the Z-axis. A plurality of positions and directions are calculated, and thereby, the insertion path diagram 71 as shown by reference numeral 9-2 of FIG. 9 is created and displayed. Subsequently, as shown by reference numeral 9-2 of FIG. 9, the pipe shape e corresponding to the design drawing of the object to be examined is superimposed on the insertion path f of the insertion path diagram 71 and displayed.

When the moving image is reproduced, the image pickup section position indicator g is displayed in the position on the insertion path f of the insertion path diagram 71 corresponding to the position at which the display image is photographed. This provides the advantage that at which position of the pipe that is the object to be examined and from which direction the displayed image is photographed can be easily grasped according to the position of the indicator g.

Meanwhile, the movable slider 52 which is placed on the reproduction bar 53 indicating the reproduction time axis in the image display region 9-1 is moved laterally with use of a key operation (or a mouse cursor) for the slider 52, and the slider 52 is placed at a certain position on the reproduction bar 53, whereby the moving image frame 51 at the time lapse point corresponding to the position of the slider is displayed, and at the same time, the image pickup section position indicator g on the insertion path f in the insertion path diagram display region 9-2 is also moved to the position on the insertion path f corresponding to the displayed moving image frame 51, and displayed. Thereby, the image of a desired site of the object to be examined (for example, a pipe) is displayed in the image as the moving image frame, and at the same time, the image pickup section position indicator g on the insertion path f plotted along the shape of the object to be examined also can simultaneously move to the corresponding position and can be displayed, whereby inspection of the inside of the pipe line excellent in operability, visibility and convenience can be carried out.

The PC 16 may be configured to have the functions of the respective units of the image synthesizing unit 11, the graphic generating unit 10, the main control unit 13 and the recording medium reading and writing unit 12 except for the moving image file generating section.

According to the present embodiment, the endoscopic image reproducing apparatus can be realized, with which it can be easily grasped that an image at a certain time point in a moving image is a result of photographing which portion of an object to be examined from which direction.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscopic image reproducing apparatus, comprising:
    an image generating unit that generates image data based on an image pickup signal picked up by an image pickup section that picks up an image of an object to be examined by an optical system and an image pickup device that are provided in a distal end of an endoscope insertion portion;
    a moving image file generating section that generates a moving image file by successively recording in a storage medium both the image data generated by the image generating unit and acceleration data measured by an acceleration measuring section that measures triaxial accelerations of the image pickup section;
    a reading section that reads the image data and the acceleration data from the moving image file that is recorded in the storage medium;
    a calculating section that calculates a position and a direction of the image pickup section at a certain time point of a moving image based on the acceleration data;
    an associating section that associates the calculated position and direction of the image pickup section at the certain time point of the moving image with the image data at the time point; and
    an insertion path calculating section that calculates an insertion path in a certain range of the moving image based on the position of the image pickup section that the calculating section calculates.

2. The endoscopic image reproducing apparatus according to claim 1, the endoscopic image reproducing apparatus further comprising:
    an insertion path diagram generating section that generates an insertion path diagram representing the insertion path and the direction of the image pickup section on the insertion path; and
    a first display control section that displays the insertion path diagram.

3. The endoscopic image reproducing apparatus according to claim 2, the endoscopic image reproducing apparatus further comprising:
    an image reproducing section that reproduces a moving image or image data in the moving image; and
    a second display control section that acquires, with the associating section, the position and the direction of the image pickup section at a time point at which the image data is photographed in correspondence with the image data reproduced at an image reproducing time, and displays both the image data and the insertion path diagram.

4. The endoscopic image reproducing apparatus according to claim 2, the endoscopic image reproducing apparatus further comprising:
    a position specifying section that specifies a certain position on the insertion path; and
    a third display control section that displays image data associated with the position.

5. The endoscopic image reproducing apparatus according to claim 2, the endoscopic image reproducing apparatus further comprising:
    a fourth display control section that displays both the insertion path generated by the insertion path diagram generating section and a design drawing showing a shape of the object to be examined.

* * * * *